United States Patent [19]
Davis et al.

[11] Patent Number: 6,159,182
[45] Date of Patent: *Dec. 12, 2000

[54] REUSABLE CANNULA WITH DISPOSABLE SEAL

[75] Inventors: John Davis, Mountain View; Tim J. Kovac, Los Gatos; Thomas Kramer, San Carlos; Bryan Loomas, Santa Clara; John To, Sunnyvale, all of Calif.

[73] Assignee: Applied Medical Resources Corporation, Laguna Hills, Calif.

[*] Notice: This patent is subject to a terminal disclaimer.

[21] Appl. No.: 09/083,772

[22] Filed: May 22, 1998

Related U.S. Application Data

[63] Continuation of application No. 08/661,760, Jun. 11, 1996, Pat. No. 5,820,606.

[51] Int. Cl.⁷ .................................................. A61M 5/178
[52] U.S. Cl. ............................. 604/167.06; 604/167.03; 604/256
[58] Field of Search ................................... 604/164, 167, 604/169, 246, 249, 256, 264, 164.01, 167.01–167.04, 167.06

[56] References Cited

U.S. PATENT DOCUMENTS

| | | |
|---|---|---|
| 1,241,352 | 9/1917 | Doering et al. . |
| 4,000,739 | 1/1977 | Stevens ................................ 128/214.4 |
| 4,240,411 | 12/1980 | Hosono ........................................ 128/4 |
| 4,653,477 | 3/1987 | Akui et al. .................................. 128/4 |
| 4,655,752 | 4/1987 | Honkanen et al. ...................... 604/256 |
| 4,673,393 | 6/1987 | Suzuki et al. ........................... 604/167 |
| 4,909,798 | 3/1990 | Fleischhacker et al. ................ 604/256 |
| 4,917,668 | 4/1990 | Haindl ..................................... 604/167 |
| 5,092,857 | 3/1992 | Fleischhacker ......................... 604/256 |
| 5,104,383 | 4/1992 | Shichman ................................ 604/167 |
| 5,141,498 | 8/1992 | Christian ................................. 604/167 |
| 5,242,412 | 9/1993 | Blake, III ................................ 604/167 |
| 5,263,944 | 11/1993 | Vidal et al. ............................. 604/256 |
| 5,269,763 | 12/1993 | Boehmer et al. ....................... 604/167 |
| 5,290,245 | 3/1994 | Dennis .................................... 604/167 |
| 5,368,574 | 11/1994 | Antonacci et al. ..................... 604/164 |
| 5,383,860 | 1/1995 | Lau ......................................... 604/167 |
| 5,385,560 | 1/1995 | Wulf ....................................... 604/264 |
| 5,397,314 | 3/1995 | Farley et al. ........................... 604/256 |
| 5,460,615 | 10/1995 | Storz ....................................... 604/167 |
| 5,496,280 | 3/1996 | Vandenbroek et al. ................ 604/167 |
| 5,549,565 | 8/1996 | Ryan et al. ............................. 604/167 |

FOREIGN PATENT DOCUMENTS

| | | |
|---|---|---|
| 0 316 096 | 5/1989 | European Pat. Off. ......... A61M 5/14 |
| 0 551 017 A1 | 7/1993 | European Pat. Off. ....... A61M 39/02 |
| 2 284 303 | 4/1976 | France ............................. A61B 1/00 |
| 3532560A1 | 3/1986 | Germany ...................... A61B 17/32 |
| WO 91/12838 | 9/1991 | WIPO .......................... A61M 5/178 |
| WO 94/19052 | 9/1994 | WIPO .......................... A61M 39/00 |

*Primary Examiner*—Corrine McDermott
*Attorney, Agent, or Firm*—Richard L. Myers

[57] ABSTRACT

A disposable seal assembly for use with a reusable cannula, where the seal assembly is designed for use with the cannula during a single medical procedure and the cannula is designed for multiple uses (each time with a different seal assembly) during a number of medical procedures. The seal assembly includes both a flapper valve fluid seal (for sealing the cannula when no medical instrument is inserted through the seal assembly) and at least one instrument seal (for sealing the cannula when a medical instrument is inserted through the seal assembly). Preferably, the seal assembly has a body with a flange which can be snapped onto the cannula before use, and readily removed after use. Also preferably, the flapper valve has an over-centered hinge. In other embodiments, the invention is a seal assembly which includes at least one double instrument seal including a sacrificial flange and a sealing flange, and optionally also a flapper valve. The sealing flange seals the cannula when a medical instrument is inserted through the seal assembly even when the sacrificial flange has been cut during insertion of the instrument. In other embodiments, the invention is a system including a reusable cannula, and a disposable seal assembly of any of the described types which can be snapped onto the cannula before use and readily removed after use.

27 Claims, 9 Drawing Sheets

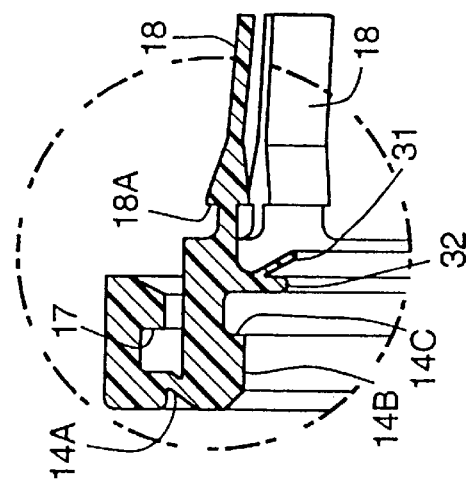
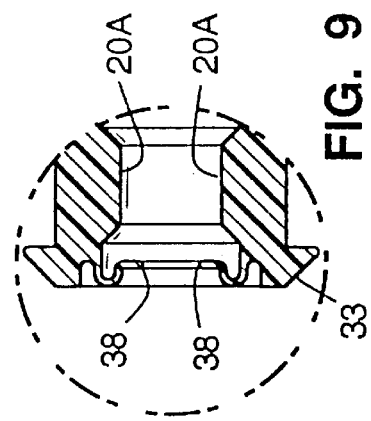
FIG. 8
FIG. 9
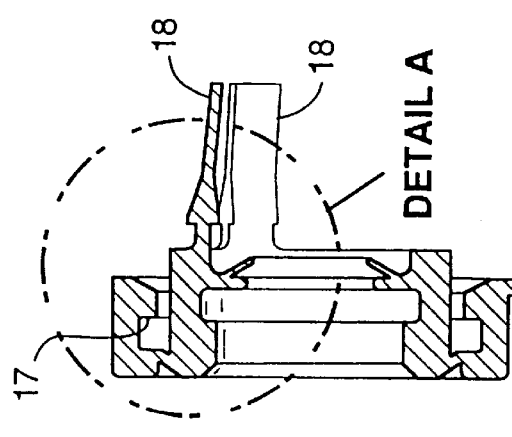
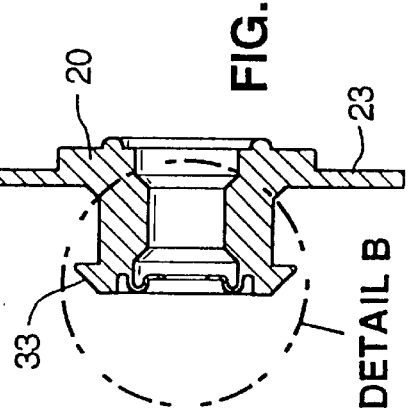
FIG. 7

REUSABLE CANNULA WITH DISPOSABLE SEAL

CROSS-REFERENCE TO RELATED APPLICATIONS

This application is a continuation of U.S. patent application Ser. No. 08/661,760, filed on Jun. 11, 1996, issued to Davis et al. on Oct. 13, 1998, as U.S. Pat. No. 5,820,606, and entitled "Reusable Cannula with Disposable Seal".

FIELD OF THE INVENTION

The invention pertains to a disposable seal assembly for use with a reusable cannula. The seal assembly is designed to be removably snapped onto the cannula for use during a single medical procedure (such as a laparoscopic procedure) and the cannula is designed for multiple use (each time with a different seal assembly) during multiple medical procedures. The seal assembly includes at least one instrument seal (for preventing fluid flow out from the cannula when a medical instrument is inserted through the seal assembly), and preferably also a flapper valve fluid seal (for sealing the cannula when no medical instrument is inserted through the seal assembly).

BACKGROUND OF THE INVENTION

Many medical procedures require use of a cannula, through which one or more medical instruments are inserted into a patient and then removed from the patient.

For example, in a variety of laparoscopic medical procedures (including laparoscopic hernia repair), a cannula is positioned with its distal end inside the patient and its proximal end outside the patient, and one or more medical instruments are inserted through the cannula into the patient. For example, each of a sequence of instruments (including an endoscope) can be inserted through the cannula into the patient and then withdrawn (in the opposite direction) out from the patient and cannula.

During many such procedures, it is necessary to maintain an insufflated working space within the patient (by maintaining insufflating gas at sufficiently high pressure in the working space) while the distal end of the cannula extends into the working space. For use during these procedures, the cannula must be provided with a seal or seals for preventing undesired fluid escape from within the patient out through the cannula. The term "fluid" is used herein to denote either a gas or a liquid. One such seal (denoted herein as a "fluid" seal) prevents fluid escape from the cannula when no instrument occupies the cannula's channel. A fluid seal is implemented as a flapper valve, duckbill valve, or other valve, which is biased in a closed position at times when no instrument occupies the cannula's channel to provide a fluid seal preventing fluid flow through the channel at such times. When the distal end of an instrument is inserted into the channel and the instrument is advanced through the channel toward the patient, the instrument opens the fluid seal (e.g., by displacing the flexible slits of a duckbill valve or displacing the trap door of a flapper valve).

Typically also, an additional seal (sometimes denoted herein as an "instrument seal") is employed in a cannula to provide a fluid seal around the instrument's outer periphery, to prevent fluid flow through the space between the instrument and the wall of the channel.

Typical prior art cannulae have had a complicated design with a built-in fluid seal and usually also an instrument seal. Such cannulae were expensive to manufacture. They were also difficult to clean after use, since contaminants often coated or became lodged in those small valve and seal parts which were in fluid communication with the cannula channel or the instrument inserted through the cannula. Often, the design of such a cannula was further complicated by the need for a mechanical linkage for manually controlling the flapper valve (e.g., to enable sufficient manual force to be applied on the linkage by a user to open the flapper valve in cases where sufficient force could not be exerted directly on the valve by an instrument without damaging the valve, another component of the cannula, or the instrument, or to enable the flapper valve to be opened for cleaning or the like).

For example, U.S. Pat. No. 5,104,383, issued Apr. 14, 1992, describes a cannula having a built-in flapper valve, and a removable "adaptor seal" which provides an instrument seal for an instrument of a first diameter. The adaptor seal can be removed and replaced by another adaptor seal which provides an instrument seal for an instrument of a second diameter.

For another example, U.S. Pat. No. 5,385,560, issued Jan. 31, 1995, describes a cannula having a built-in flapper valve, and a built-in instrument seal for an instrument having a relatively large diameter. A "reducer" member snaps on the end of the cannula, to provide an instrument seal for an instrument (having a relatively small diameter) which may be inserted through the cannula.

For another example, U.S. Pat. No. 5,290,245, issued Mar. 1, 1994, describes a cannula having several threaded portions which are assembled by being screwed together. The cannula includes a flapper valve mounted on one of the portions and an instrument seal mounted on another of the portions.

It has been proposed to design a cannula to have a distal portion (for insertion in a patient), and a proximal portion which is removably attachable to the first portion and which includes a fluid seal. For example, U.S. Pat. No. 5,460,615, issued Oct. 24, 1995 to Karl Storz, discloses (with reference to FIGS. 4–7) a cannula having a distal portion (with a trocar sleeve and a valve housing) and a proximal portion (with a flapper valve, a first instrument seal, and a second instrument seal attached by a tether to the first instrument seal). A bayonet closure is provided for removably attaching the proximal portion to the distal portion. However, the proximal portion has a complicated structure, it would be expensive to manufacture, and it is not intended to be used once and then discarded.

It had not been known until the present invention how to design a cannula assembly with a simple reusable cannula, and a simple disposable seal (including both a flapper valve fluid seal and at least one instrument seal) which can be snapped onto the cannula and then readily removed after use.

SUMMARY OF THE INVENTION

In a class of preferred embodiments, the invention is a disposable seal assembly for use with a reusable cannula, where the seal assembly is designed for use with the cannula during a single medical procedure (such as a laparoscopic procedure) and the cannula is designed for multiple uses (each time with a different seal assembly) during a number of medical procedures. A channel extends through the seal assembly, and the seal assembly includes both a flapper valve fluid seal (for sealing the cannula when no medical instrument is inserted through the seal assembly) and at least one instrument seal (for sealing the cannula when a medical instrument is inserted through the seal assembly). Preferably, the seal assembly has a body with a flange which can be snapped onto the cannula (so that the flange fits in a groove of the cannula) before use, and can be readily removed from the cannula after use. The seal assembly is preferably molded from an elastomeric material (e.g., rubber), except for the trap door of its flapper valve. In preferred embodiments, the trap door is molded from a rigid material (e.g., a rigid plastic), and is mounted to the elastomeric portion of the assembly. This simple design makes the assembly inexpensive to manufacture and thus disposable. Alternatively, the entire seal assembly (including a trap door portion thereof) can be molded from an elastomeric material (e.g., rubber).

Preferably, the trap door is mounted on an over-centered door hinge designed to reduce the drag force exerted by the opened door on an instrument, as the instrument translates past (and displaces) the door. The door preferably has slits extending through it, and the over-centered hinge preferably includes appropriately shaped extensions of the seal assembly's elastomeric portion which are inserted through the slots to mount the door. Each extension typically has a barb (for retaining the door after the end portion of the extension and the barb have been inserted through a slot through the door), and thus the extensions are sometimes denoted herein as "barbed portions."

Preferably, the trap door is mechanically joined to (e.g., molded with) flexible extensions of the seal assembly's elastomeric portion so that, if the door becomes improperly positioned, the extensions exert restoring force on the door thereby repositioning the door properly. Alternatively, direct manual force exerted by a user on the door together with restoring force exerted by the extensions on the door, is sufficient to reposition the door if it becomes improperly positioned.

Preferably, the channel has a first radius at a first end of the seal assembly's body, and there is a bumper along the channel (away from the first end) having a smaller radius (with respect to the central longitudinal axis of the channel) than the first radius. The bumper, which is preferably a molded portion of the seal assembly's body, functions to limit lateral movement of an instrument extending through the channel. Preferably, when the seal assembly is mounted to the cannula, the bumper is positioned so that the cannula bears at least part of the load exerted on the bumper by the instrument (to limit undesired deformation of the elastomeric portion of the seal assembly).

In preferred embodiments, the seal assembly includes a main portion and an adaptor portion. The flapper valve is mounted to the main portion, the main portion includes an instrument seal for use with a relatively large diameter instrument, and the adaptor portion includes an instrument seal for use with a smaller diameter instrument, and preferably also a bumper. Preferably the main and adaptor portions are connected by a tether portion, and all three portions (including the bumper of the adaptor portion) are a single molded piece of elastomeric material.

In other embodiments, the invention is a seal assembly including at least one double instrument seal, comprising a sacrificial flange and a second sealing flange (for sealing the cannula when a medical instrument is inserted through the seal assembly even when the sacrificial flange has been cut during insertion of the instrument). In preferred embodiments, the seal assembly includes a flapper valve fluid seal as well as such a double instrument seal.

In other embodiments, the invention is a cannula system including a reusable cannula, and a disposable seal assembly (of any of the described types) which can be snapped onto the cannula before use and readily removed after use. The cannula of such a system preferably includes no fluid seal or instrument seal, and thus is easy to clean after use. In other embodiments, the invention is a method for using such a cannula system.

BRIEF DESCRIPTION OF THE DRAWINGS

FIG. 7 is a side cross-sectional view of disposable seal 2 of FIG. 1.

FIG. 8 is an enlarged view of the portion of FIG. 1 labeled "Detail A."

FIG. 9 is an enlarged view of the portion of FIG. 1 labeled "Detail B."

DETAILED DESCRIPTION OF THE PREFERRED EMBODIMENT

A preferred embodiment of the invention will be described with reference to FIGS. 1–9 and 14. Other embodiments will be described with reference to FIGS. 10–13 and 15–20.

Figure 1:
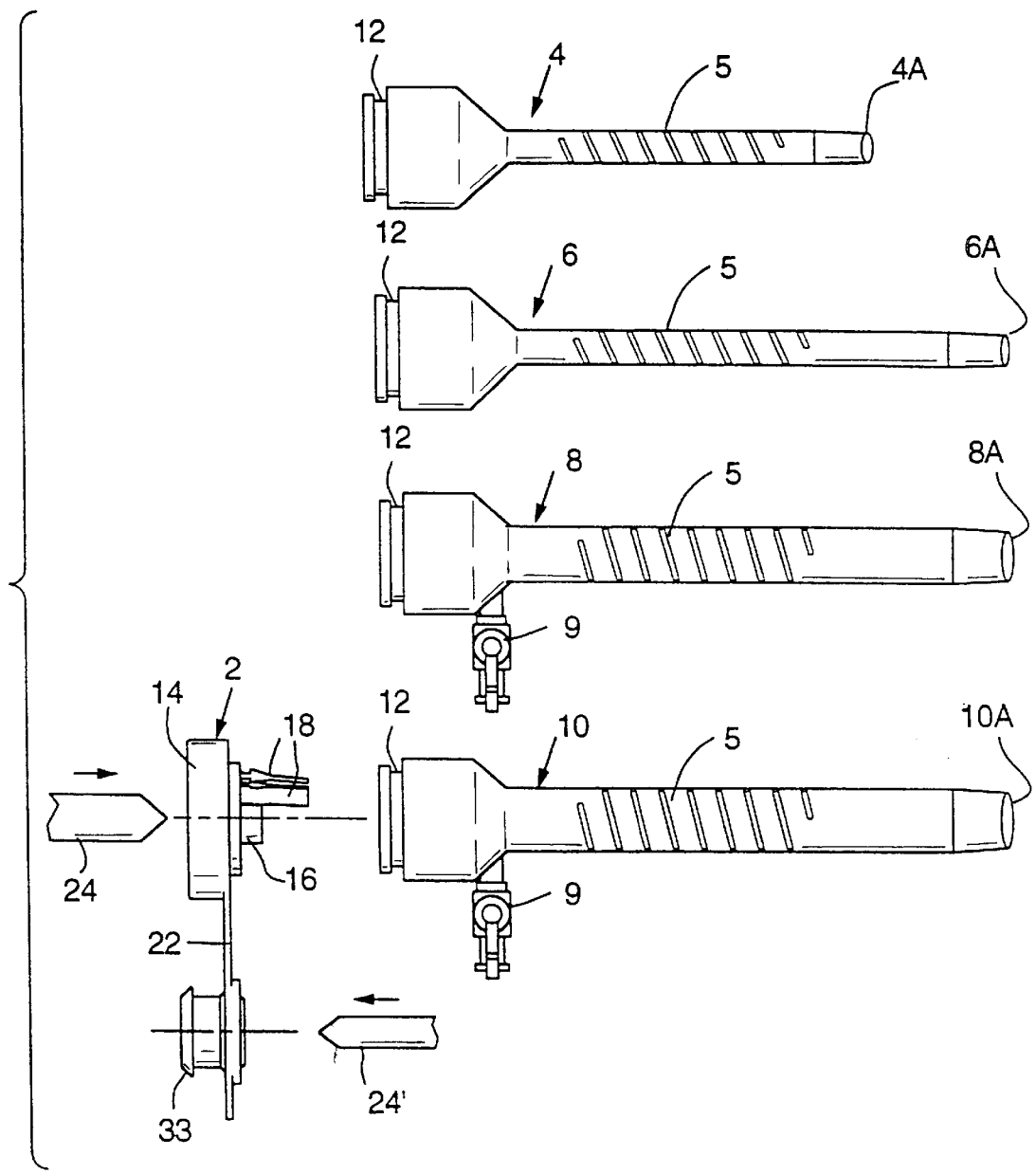
FIG. 1 is a side elevational view of a disposable seal and four reusable cannulae (each cannula usable with the seal) according to a preferred embodiment of the invention.

As shown in FIG. 1, seal assembly 2 is a preferred embodiment of the inventive disposable seal, and each of cannula 4, cannula 6, cannula 8, and cannula 10 is an embodiment of the inventive reusable cannula. Each of cannulae 4, 6, 8, and 10 has a distal end (end 4A, 6A, 8A, and 10A, respectively) which is inserted within a patient during use, and a proximal end opposite the distal end. Each cannula has a central longitudinal channel extending through it, and any of a variety of instruments (such as relatively small diameter instrument 24' which can be an obturator or endoscope) can be positioned in the channel while the cannula is inserted into the patient (or after the cannula has been inserted into the patient). The outer wall of each cannula (each cannula is preferably made of a rigid material such as metal or rigid plastic) has a grip portion 5. Preferably, grip portion 5 produced by scoring a pattern (e.g., a spiral pattern as shown in FIG. 1) into the outer metal surface of the cannula. Alternative embodiments of the cannula have no grip portion, and instead the outer wall of each is smooth.

The proximal end of each cannula is identically shaped and sized, so that seal assembly 2 can be snapped onto any of them. More specifically, the proximal end of each of cannulae 4, 6, 8, and 10 is generally cylindrical, and has an identical annular groove 12 around it. A flange portion (flange 17, shown in FIG. 2 but not in FIG. 1) of body portion 14 of seal assembly 2 can be snapped into groove 12 to removably attach seal assembly 2 onto any of the cannulae. Preferably, body 14 has a thin annular portion 14a (shown in FIG. 2) between flange 17 and the main portion of body 14. The thin portion 14a (which has a thickness of 0.03 inches in one embodiment) functions as a bellows allowing flange 17 to flex relative to the main portion of body 14, so that assembly 2 can be manipulated by a user without removing flange 17 from groove 12.

Figure 14:
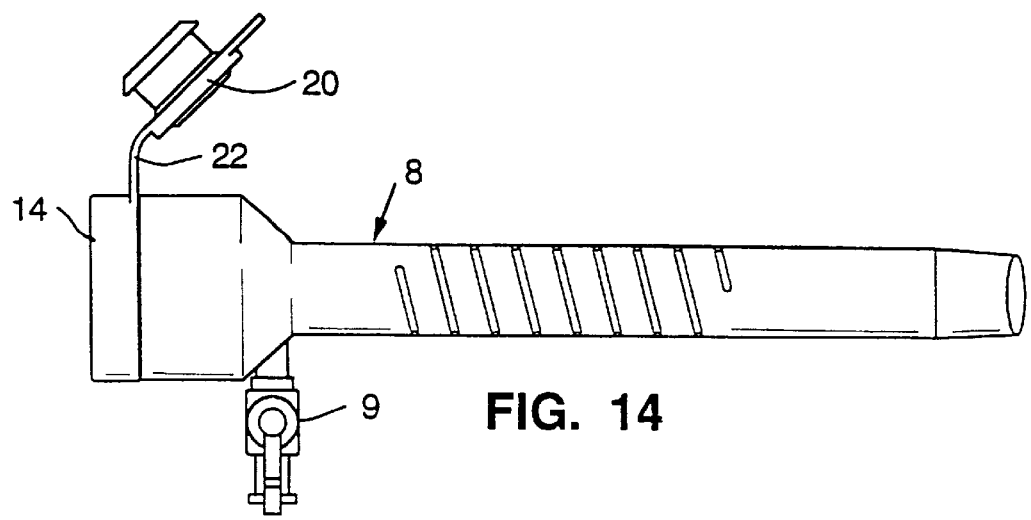
FIG. 14 is an elevational view of reusable cannula 8 (of FIG. 1), with seal 2 (of FIG. 1) snapped onto the proximal end of the cannula, and a stopcock 9 mounted to the cannula.

FIG. 14 is an elevational view of cannula 8, with body portion 14 of assembly 2 snapped onto the proximal end of cannula 8, and adaptor portion 20 of seal 2 connected to body portion by tether 22.

As shown in both FIG. 1 and FIG. 14, stopcock 9 is mounted to an orifice (not shown in FIG. 1 or 14, but identical to orifice 101 shown in FIGS. 12 and 13) which extends through cannula 8. A source of insufflation gas can be connected to stopcock 9 at desired times during a medical procedure, and stopcock 9 can be opened (to allow gas to flow through the orifice into or out from cannula 8) or closed (to seal the orifice). FIG. 1 shows an identical stopcock 9 mounted to cannula 10. Some embodiments of the inventive reusable cannula have an orifice to which a stopcock can be mounted, while others (e.g., cannula 4) do not have such an orifice.

Preferably, seal 2 is molded from elastic material (such as medical grade silicon rubber or another medical grade elastomer), except for its rigid trap door 16 (which can be molded from hard plastic such as polycarbonate material). Thus, seal has a simple design consisting of two components only. In alternative embodiments, the trap door is made of non-rigid material. In some such alternative embodiments, to be described below with reference to FIG. 20, the inventive seal is molded as a single piece of elastomeric material (including an elastomeric trap door portion). Cannulae 4, 6, 8, and 10 are preferably made of rigid such as stainless steel (or another metal) or rigid plastic.

Two flexible extension portions 18 protrude out from body portion 14 of seal 2, and trap door 16 is mounted on members 18. Preferably, each extension portion 18 has a barb 18a for retaining the door against body portion 14 after the extension portion's head (which preferably has a generally triangular cross-section) and the barb have been inserted through a slot through the door, and each extension portion 18 also has a flexible shaft connecting the head to body portion 14. Thus, each extension portion 18 will sometimes be denoted herein as an "barbed portion"), although it is contemplated that flexible extensions having other shapes can be used in alternative embodiments of the invention.

Body portion 14 has a trap door seat portion (flange 31 shown in FIG. 2 but not in FIG. 1) which surrounds the distal end of the central channel 15 (shown in FIGS. 5 and 6) which extends through body portion 14. Central channel 15 extends along central longitudinal axis Z of seal 2 (shown in FIG. 2), and preferably has rotational symmetry about axis Z.

Trap door 16 is biased by barbed portions 18 so that it normally rests in a closed position against the trap door seat, so that the closed trap door 16 prevents fluid from flowing through central channel 15. Trap door 16, barbed portions 18, and the trap door seat portion comprise a flapper valve, which functions as follows. Barbed portions 18 are flexible so that when seal 2 has been snapped onto a cannula and an instrument (e.g., relatively large diameter instrument 24 of FIG. 1) is inserted through the central channel through body portion 14 (and through the trap door seat and into the channel extending through the cannula), the instrument displaces trap door 16 away from the trap door seat (thereby bending barbed portions 18) and continues into the cannula's channel (until the distal end of the instrument passes entirely through the channel and out the distal end of the cannula). Then, when the instrument is withdrawn from the cannula and seal 2, barbed portions 18 relax, thus urging trap door 16 back into its normal position preventing fluid flow past the trap door seat.

Preferably also, body 14 includes an instrument seal portion (flanges 31 and 32, to be described below) which prevents fluid flow past an instrument which has been inserted through seal 2. Typically, such instrument seal portion is a simple flange (or double flange of a type to be described below) which extends into a central channel through seal 2. Because such a flange (or double flange) has a fixed diameter, it will not provide a good seal around instruments having diameter less than a particular value. Thus, adaptor portion 20 of seal 2 is provided, so that adaptor portion 20 (attached to body portion 14 by flexible tether 22) can be snapped onto body portion 14 to adapt the seal for use with a smaller diameter instrument. Adaptor 20 has an instrument seal portion which can be a simple flange (e.g., flange 38 shown in FIGS. 5, 6, and 9) or a double flange (including a sacrificial flange and a seal flange) which extends into a central channel through adaptor 20, for providing a good seal around instruments having a range of relatively small diameters. For example, when seal assembly 2 is snapped onto the end of large diameter cannula 10, relatively large diameter instrument 24 can be inserted through body 14, and the instrument seal within body 14 provides a good fluid seal around instrument 24. If the user desires to insert an instrument having substantially smaller diameter than instrument 24 (e.g., relatively small diameter instrument 24') into cannula 10, the user snaps adaptor 20 onto body 14 (so that the central channels through body 14 and adaptor 20 are aligned) and then inserts the relatively small diameter instrument through adaptor 20. When the relatively small diameter instrument (e.g., instrument 24') is so inserted through adaptor 20 (and body 14) into cannula 10, the instrument seal within adaptor 20 provides a good fluid seal around the relatively small diameter instrument, and the relatively small diameter instrument displaces door 16 of the flapper valve within body 14.

It is contemplated that any of a variety of variations on disposable seal 2 can be used interchangeably with any of the cannulae. Each such variation is a disposable seal having at least one instrument seal (useful with instruments having a particular outer diameter or range of outer diameters) and a flapper valve.

In one embodiment, each of short cannula 4 and long cannula 6 has a channel of diameter slightly greater than 5 mm (for use with an instrument of 5 mm diameter), cannula 8 has a channel of diameter slightly greater than 10 mm (for use with an instrument of 10 mm diameter), and cannula 10 has a channel of diameter slightly greater than 12 mm (for use with an instrument of 12 mm diameter). For use with all such cannulae and instruments, adaptor portion 20 of seal 2 can include an instrument seal of a diameter which provides a seal around an instrument of 5 mm diameter, and body portion of seal 2 can include an instrument seal of a diameter which provides a seal around an instrument having any diameter in the range from 10 mm to 12 mm.

Figures 2, 3, 4:
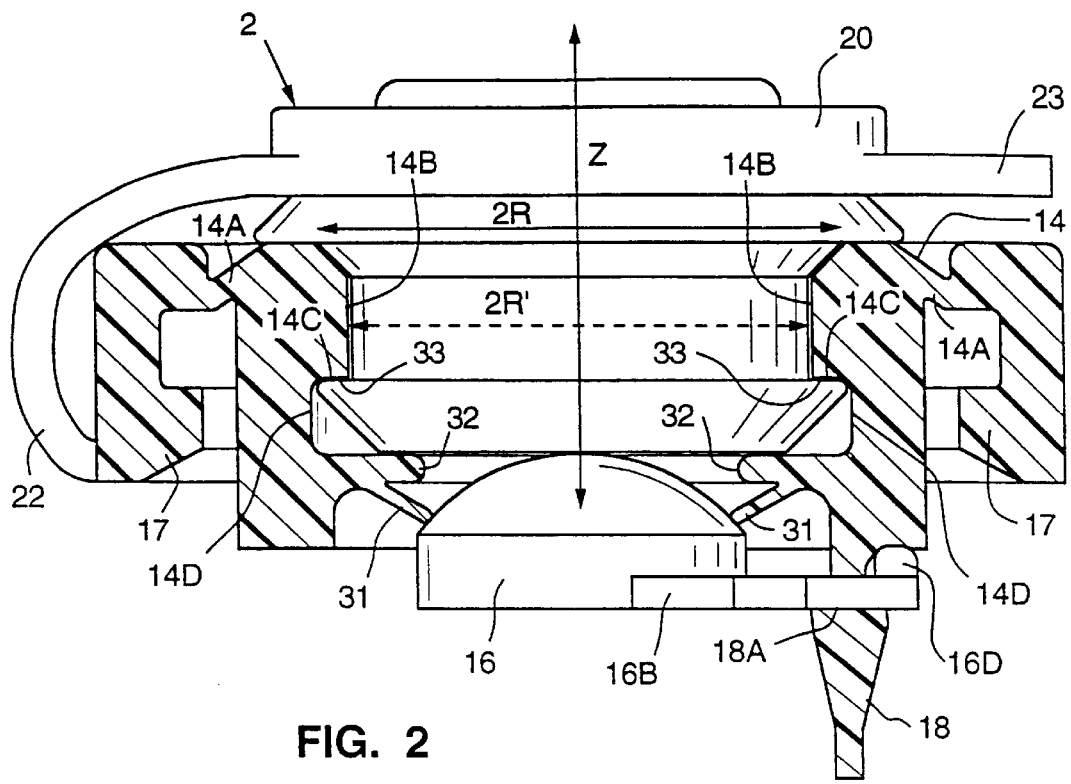
FIG. 2 is a side cross-sectional view of disposable seal 2 of FIG. 1, in a configuration in which adaptor portion 20 has been snapped onto body portion 14.
FIG. 3 is a top elevational view of trap door 16 of disposable seal 2 of FIG. 1.
FIG. 4 is a side elevational view (partially cut away) of trap door 16 of disposable seal 2 of FIG. 1.
Figure 5:
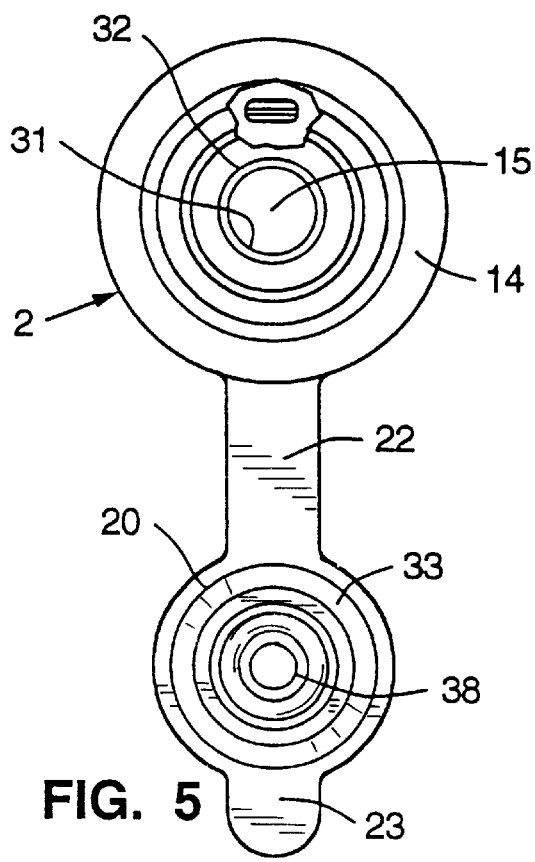
FIG. 5 is a top view (partially cut away to show the location of one of barbed portions 18) of disposable seal 2 of FIG. 1 (without trap door 16).
Figure 6:
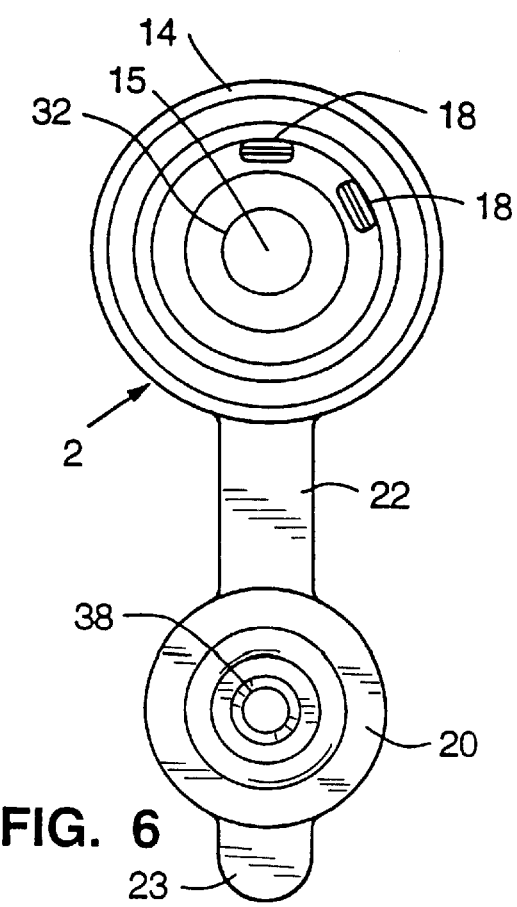
FIG. 6 is a bottom view of disposable seal 2 of FIG. 1 (without trap door 16).

With reference to FIG. 2, adaptor portion 20 of seal 2 has a distal end surrounded by a circular flange 33. Adaptor portion 20 can be snapped onto body 14 by inserting its distal end into the central channel through body 14 until flange 33 translates past shoulder 14c of body 14 into groove 14d of body 14, as shown in FIG. 2. With flange 33 in this position, shoulder 14c locks adaptor portion 20 in place, preventing flange 33 from translating in the proximal direction (toward the top of FIG. 2) until a user grips body 14 (to hold body 14 in a fixed position) and exerts manual force (in the proximal direction) on one side of adaptor 20, such as by pulling up on flap 23 of adaptor 20.

Trap door 16 is mounted on barbed portions 18 of body 14 (shown in FIGS. 2, 6, 7, and 8). Trap door 16 has a generally hemispherical portion which rests against flange 31 when the flapper valve is in its closed position shown in FIG. 2. Trap door 16 also has a flange 16B, and two slots 16A extend through flange 16B (as shown in FIGS. 3 and 4). Trap door 16 is mounted to body 14 by inserting one barbed portion 18 through each slot 16A until shoulder 18a (of each barbed portion) passes through slot 16A, and spacer portion 16D of door 16 abuts body 14. Thus, each barbed portion 18 is slightly stretched by the force exerted on shoulder 18a by door 16, and barbed portions 18 in turn exert a biasing force on door 16 tending to keep door 16 in the closed position against the trap door seat (as shown in FIG. 2). As the hemispherical portion of door 16 is displaced away from the trap door seat (by an instrument which pushes the hemispherical portion as the instrument translates through the central channel of body 14), barbed portions 18 will bend and also stretch, thus allowing door 16 and barbed portions 18 to pivot away from the instrument (together as a unit about spacer 16D).

The biasing torque exerted by barbed portions 18 on door 16 (tending to keep door 16 in the closed position shown in FIG. 2) is T=2PX, where P is the preload force exerted (toward the top of FIG. 2) on door 16 by each barbed portion 18, and X is the distance (shown in FIG. 2) between the center of spacer 16D and the central longitudinal axis of each barbed portion 18. Since X is greater than zero, door 16 is said to be mounted on an "over-centered" door hinge.

As door 16 is displaced (by an instrument) into its open position, barbed portions 18 will bend and stretch, and the distance between spacer 16D and the central axis of each barbed portion will be reduced to a value X' (where X' is less than X) as spacer 16D slides slightly to the left in FIG. 2). This effect tends to reduce the torque on door 16. The torque exerted by barbed portions 18 on door 16 (when door 16 is in its opened position) is T=2P'X'+M, where M is the moment due to the bending of barbed portions 18, and P' is the increased preload force exerted on door 16 by each barbed portion 18 (P' is greater than P since barbed portions 18 become stretched, that is elongated, when door 16 is in its opened position). Door 16 and barbed portions 18 are designed so that no more than an acceptable maximum torque is exerted on door 16 by barbed portions 18, regardless of the angle by which door 16 is rotated (about its pivot point) from its closed orientation (e.g., so that the torque reduction caused by the reduced factor X' cancels a sufficient amount of the torque increase due to the parameters P' and M). If the torque exerted on door 16 (by barbed portions 18) is so controlled, the opened door 16 will exert no more than an acceptable amount of drag force on any instrument being translated through channel 15 into (or out from) the cannula to which seal 2 is connected.

More generally, the trap door of the inventive seal is preferably mounted on an over-centered door hinge, such that the change in torque applied by the seal to the door relative to the change in the orientation angle of the door decreases with increasing pivoting displacement of the door away from its closed orientation (i.e., such that $d^2T/dA^2$ is negative, where T is the applied torque and A is the door's orientation angle relative to the orientation angle of the closed door).

Also to reduce the drag force exerted by the opened door on the instrument displacing the door, the door surface which engages the instrument should be a smooth, hard surface (for reduced friction).

In alternative embodiments of the invention, only one barbed portion is used to attach the trap door to the body of the inventive seal. In this case, the trap door would have only a single slot, rather than dual slots 16A as shown in FIG. 3. To ensure stable positioning of the door, such a single barbed portion would typically be wider than barbed portions 18 shown in FIGS. 2 and 6–8, in the sense that it would extend farther around the periphery of channel 15 than does either of barbed portions 18 (of FIGS. 2 and 6–8).

Also, in alternative embodiments of the inventive seal assembly, the trap door of the seal assembly is attached to the seal assembly's flexible extensions (which are not necessarily barbed or arrow-shaped) other than by inserting the extensions through slots in the trap door. For example, the trap door could be attached to the extensions by glue or another adhesive (in such cases, the trap door need not have a slot extending through it), or the extensions could have one or more slots extending through them and the trap door could fit through such slot or slots.

With reference to FIG. 2, we next discuss small diameter portion 14b of body 14 of seal 2, which functions as a bumper to limit lateral motion of a large diameter instrument which occupies the central channel through seal 2 (when adaptor portion 20 has been removed from its position shown in FIG. 2 within body 14). The channel has a first diameter 2R (shown in FIG. 2) and thus a first radius R at a first end of body portion 14, and bumper 14*b* has a smaller diameter 2R' (and thus a radius R', relative to the central longitudinal axis Z of the channel, which is smaller than the first radius R). Bumper 14*b* does not extend as far radially into the central channel as does flange 32 or 31 (so that it does not interfere with the sealing function of flange 31). Instead, bumper 14*b* functions to limit lateral movement of any large diameter instrument which extends through the channel (as does bumper ring 95 in the FIG. 11 embodiment described below).

Preferably, bumper 14*b* is located low enough along the longitudinal axis of seal assembly 2 so that it rests against the cannula (when assembly 2 is snapped onto the end of the cannula), allowing loads from an instrument on bumper 14*b* to be borne by the inner wall of the cannula to which assembly 2 is mounted. This preferred arrangement is in contrast with that of the FIG. 15 embodiment (to be discussed below) in which end portion 4*a* of the wall of cannula 4 (shown in FIG. 15) is below bumper 14*b*' along the vertical axis of the channel (extending through seal assembly 2' and cannula 4) with which instrument 24 is aligned, so that bumper 14*b*' of FIG. 15 does not rest directly against the wall of cannula 4, and the cannula does not directly bear an instrument load on bumper 14*b*'.

Preferably, adaptor 20 also has an instrument seal (flange 38, best shown in FIG. 9) and a bumper (bumper 20*a*, best shown in FIG. 9) for limiting lateral movement of any relatively small diameter instrument which extends through the central channel through adaptor 20. In the preferred embodiment of adaptor 20 shown in FIGS. 5–9, circular flange 38 extends sufficiently far radially into the central channel so that it provides a seal preventing fluid flow between flange 38 and the outer periphery of a relatively small diameter instrument which extends through the central channel. Bumper portion 20*a* of adaptor 20 does not extend as far radially into the central channel as does flange 38 (so that it does not interfere with the sealing function of flange 38). As noted above, adaptor 20 (designed for use with a relatively small diameter instrument) would be snapped into body 14 for use with such a relatively small diameter instrument, and adaptor 20 would not be used when a relatively large diameter instrument is to be inserted directly through body 14 into a cannula. In variations on this embodiment, the adaptor portion of the inventive seal assembly is designed to be snapped over (rather than into) the body portion thereof.

Figure 21:
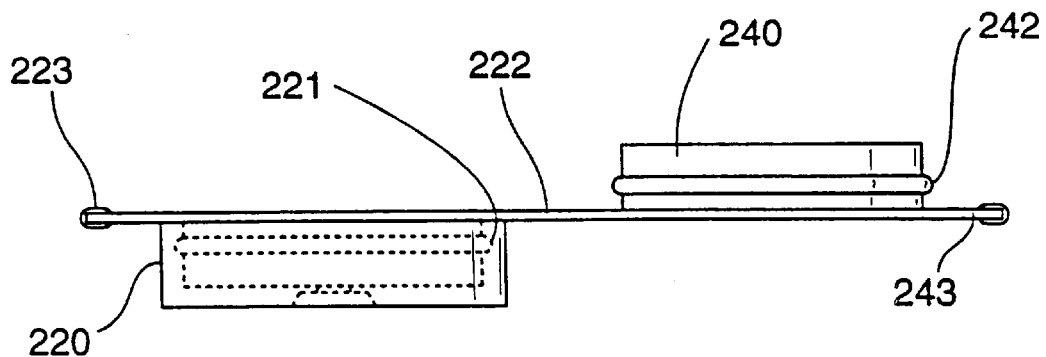
FIG. 21 is a side view, partially elevational and partially cross-sectional, of an alternative embodiment of the inventive disposable seal, which is molded as a single piece of elastomeric material.

For example, FIG. 21 is a side view of an alternative embodiment of the inventive seal, including main portion 240 and tether portion 222 (shown in elevational view) and adaptor portion 220 (shown in cross-sectional view). The seal of FIG. 21 is molded as a single piece of elastomeric material. Each of portions 220 and 240 includes an instrument seal of any of the types described herein (and portion 240 optionally also includes a flapper valve of any of the types described herein). In the configuration shown in FIG. 21, main portion 240 can be snapped onto the end of a cannula, and a relatively large diameter instrument can be inserted through main portion 240 into the cannula.

Figure 22:
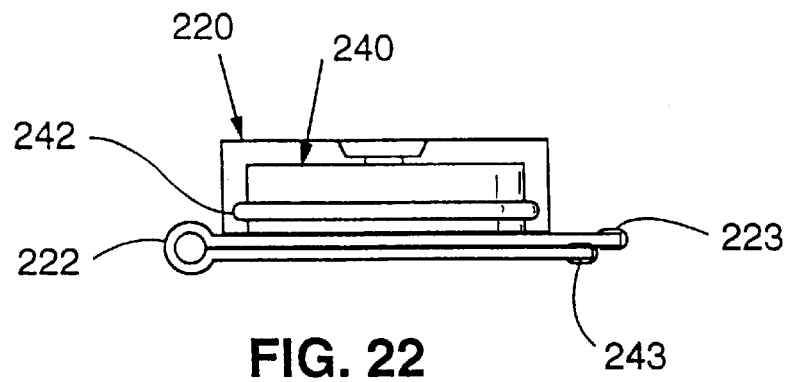
FIG. 22 is a side cross-sectional view of the seal of FIG. 21, with adaptor portion 220 snapped over main portion 240.

To adapt the FIG. 21 seal to provide a good seal around a smaller diameter instrument, adaptor portion 220 is snapped over main portion 240 as shown in FIG. 22, with ring-shaped flange 242 of portion 240 fitted into ring-shaped groove 221 of portion 220. Flexible tether portion 222 bends into the position shown in FIG. 22 as portions 220 and 240 are aligned and snapped together. In the configuration shown in FIG. 22, main portion 240 can be snapped onto the end of a cannula, and a relatively small diameter instrument can be inserted through both portion 220 and main portion 240 into the cannula. To remove portion 220 from portion 240, a user grips flap 243 of portion 240 (to hold portion 240 in a fixed position) and exerts manual force (in the proximal direction, i.e., toward the top of FIG. 22) on one side of adaptor portion 220, such as by pulling up on flap 223 of adaptor portion 220.

In other variations on the described embodiment of FIGS. 1–9, a rigid (or substantially rigid) bumper ring is installed along the central channel of the inventive seal (either above or below the position of the instrument seal). The ring should not extend as far (radially) into the channel as does the instrument seal (which is typically a thin, compliant flange) so that the ring does not interfere with the sealing function of the instrument seal. Rather, the ring functions as a bumper to limit lateral movement of any instrument extending through the channel while the instrument prevents fluid flow between the outer periphery of the instrument and the instrument seal. The ring can be a separate element which is mounted to the body of the seal assembly, or it can be an integrally molded portion of the seal assembly's body. Preferably (to reduce the drag force exerted on the instrument by the ring), the surface of the ring which meets the instrument is a smooth, hard surface.

We next discuss circular flanges 31 and 32 of body portion 14 of seal 2, which function as an instrument seal (when adaptor portion 20 has been removed from its position shown in FIG. 2 within body 14). Circular flange 32 functions as a sacrificial seal in the following sense. Flange 32 comes into contact with an instrument being inserted downward along axis Z through the central channel through seal 2 (into the cannula to which seal 2 is mounted) before thin circular flange 31 does, and if flange 32 is displaced (or even cut) by a sharp instrument being so inserted, flange 31 will maintain a good fluid seal against the instrument (preventing fluid flow between flange 31 and the outer periphery of the instrument). Preferably, flange 31 extends farther into channel 15 than does flange 32 (the radial distance between axis Z and flange 31 is less than the radial distance between axis Z and flange 32), and flange 31 is thinner than flange 32 as shown in FIGS. 2 and 8 (e.g., flange 31 is 0.005 inches thick, and flange 32 is 0.028 inches thick in one embodiment). With this preferred design, if flange 32 is displaced by an instrument (or possibly even cut by a sharp instrument) being inserted downward along axis Z, the displaced portion of flange 32 (e.g., a displaced portion of flange 32 adjacent to a cut in flange 32) will fold downward, thereby causing a portion of flange 31 temporarily to open slightly (radially away from axis Z) so that flange 31 will avoid being cut by the instrument (as the instrument continues to advance past flange 32). After flange 31 opens temporarily in this manner, flange 31 (which is made of elastomeric material) will relax back to a position sealing the outer periphery of the instrument. Flange 31 is preferably oriented at an angle relative to sacrificial flange 32 as shown (so that flange 31 extends away from sacrificial flange 32 toward the distal end of the cannula during use), to improve its ability to provide a good fluid seal with an instrument (but alternatively, flanges 31 and 32 are parallel or substantially parallel to each other). Flange 31 functions as an instrument seal as well as a trap door seat. If flange 32 is not cut by an instrument, both flanges 32 and 31 can function to seal around the outer periphery of an instrument which extends through them.

In variations on the embodiment of FIGS. 1–9 described above, the body portion of the inventive seal includes an instrument seal which is separated along the central channel from a trap door seat. For example, the seal includes a first flange (which functions as a trap door seat), and a second flange spaced along the central channel from the first flange (which functions as an instrument seal). In such variations, the trap door seat can have a different shape than flange 31 shown in FIG. 2. An advantage of such variations on the FIGS. 1–9 embodiment is that the instrument seal can be designed with dimensions that are optimal for sealing around a particular instrument to be inserted through the central channel, while the trap door seat can be designed with dimensions that are optimal for providing a fluid seal between the trap door and the trap door seat. In contrast, the embodiment of FIGS. 1–9 has the design constraint that flanges 31 and 32 must be designed to serve the dual function of a trap door seat and an instrument seal.

We next describe another advantage of the invention with reference to FIGS. 15–19. This advantage is that mounting the flapper valve on a flexible seal eliminates the need for a mechanical linkage for controlling the flapper valve. In contrast, in a conventional apparatus in which a flapper valve is permanently installed in a rigid cannula, the cannula must also be provided with a mechanical linkage which allows the user to open or close the flapper valve manually under certain conditions (such as when it becomes stuck).

Figure 15:
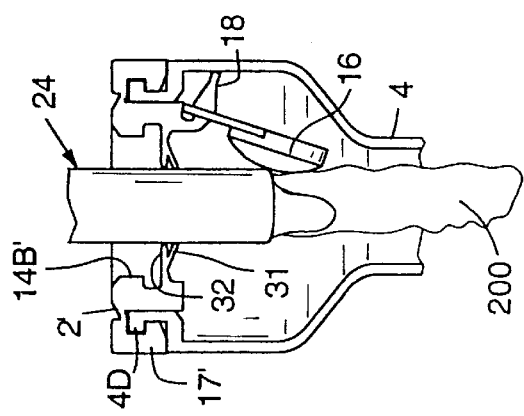
FIG. 15 is a simplified side cross-sectional view of an alternative embodiment of the inventive disposable seal snapped onto the end of cannula 4 (of FIG. 1), with a tissue specimen 200 being withdrawn by instrument 24 through the cannula from a patient.

FIG. 15 is a simplified side cross-sectional view of seal 2' (an alternative embodiment of the inventive disposable seal) snapped onto proximal end 4D of cannula 4 (of FIG. 1), with a tissue specimen 200 being withdrawn (by an instrument 24 whose distal end is within cannula 4) from a patient. Seal 2' includes trap door 16, barbed portions 18 on which door 16 is mounted, and flanges 31 and 32, all identical to the identically numbered elements of seal 2 in the above-described embodiment of FIGS. 1–9. Seal 2' differs from above-described seal 2 in that seal 2' does not include an adaptor portion, and in that bumper 14b' and flange 17' of seal 2' have slightly different shapes than do corresponding elements 14b and flange 17 of seal 2.

Figure 17:
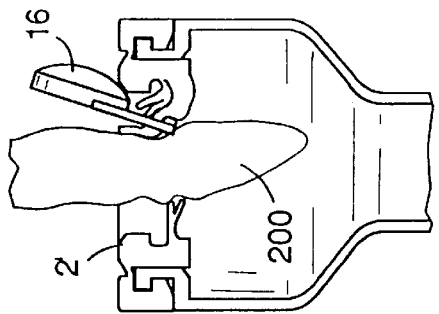
FIG. 17 is a view of the FIG. 16 apparatus, after specimen 200 has been further withdrawn from the cannula.
Figure 16:
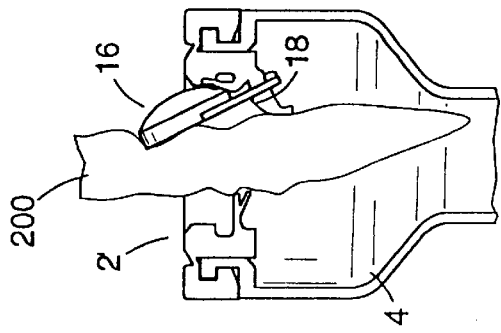
FIG. 16 is a view of the FIG. 15 apparatus, after specimen 200 has been further withdrawn from the cannula.
Figure 18:
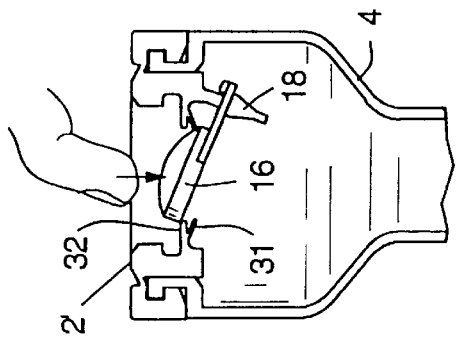
FIG. 18 is a view of the FIG. 15 apparatus, after specimen 200 has been completely withdrawn from the cannula.

FIGS. 16–18 are views of the FIG. 15 apparatus at four succeeding moments during (and after) extraction of the tissue sample from the patient.

FIG. 16 is a view of the FIG. 15 apparatus at a time when instrument 24 has been completely withdrawn from cannula 4 and seal 2', but while specimen 200 is still in the process of being withdrawn from cannula 4 and seal 2'. Specimen 200 has become snagged on door 16, and the upward force exerted by specimen 200 on door 16 has caused door 16 to bend barbed portions 18 clockwise and to stretch barbed portions 18.

As the instrument (not shown in FIG. 17) continues to pull specimen 200 upward (to the position shown in FIG. 17), barbed portions 18 have been stretched so far that door 16 is completely outside (and above) the main body of seal 2'.

Since door 16 is mounted on flexible, resilient material (all of seal 2', including barbed portions 18, except for door 16 itself), barbed portions 18 will not break (or tear) even when moved to the position shown in FIG. 17. Instead, barbed portions will relax (from the FIG. 17 position) back to the position shown in FIG. 18 after specimen 200 has been pulled away from the apparatus (so that specimen 200 no longer exerts force on door 16 or barbed portions 18. In the FIG. 18 position, door 16 rests on top of upper flange 32, rather than being properly positioned in its closed position below both flanges 31 and 32 (biased upward against flange 32 by barbed portions 18). To return door 16 to its proper closed position, a user can simply exert pressure (e.g., with his or her finger) downward on door 16 to push door 16 through flanges 31 and 32.

Figure 19:
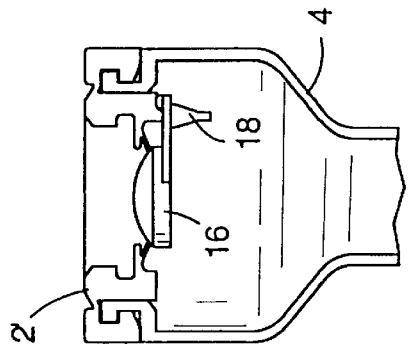
FIG. 19 is a view of the FIG. 18 apparatus, after a user has pushed trap door 16 back into the cannula.

FIG. 19 is a view of the FIG. 18 apparatus, after a user has pushed door 16 through flanges 31 and 32 so that door 16 is once again biased by barbed portions 18 to remain in its proper closed position. As will be apparent from FIGS. 15–19, neither seal 2' nor cannula 4 need be provided with a mechanical linkage for manipulating any part of the flapper valve (trap door 16, barbed portions 18, and flange 31 which functions as the trap door seat). If trap door 16 becomes improperly positioned (possibly due to an instrument or specimen snag on the door, as in FIG. 18), the simple design of seal 2' prevents seal 2' from tearing (when door 16 becomes improperly positioned) and allows a user to exert direct manual force on door 16 to reposition it.

Figure 20:
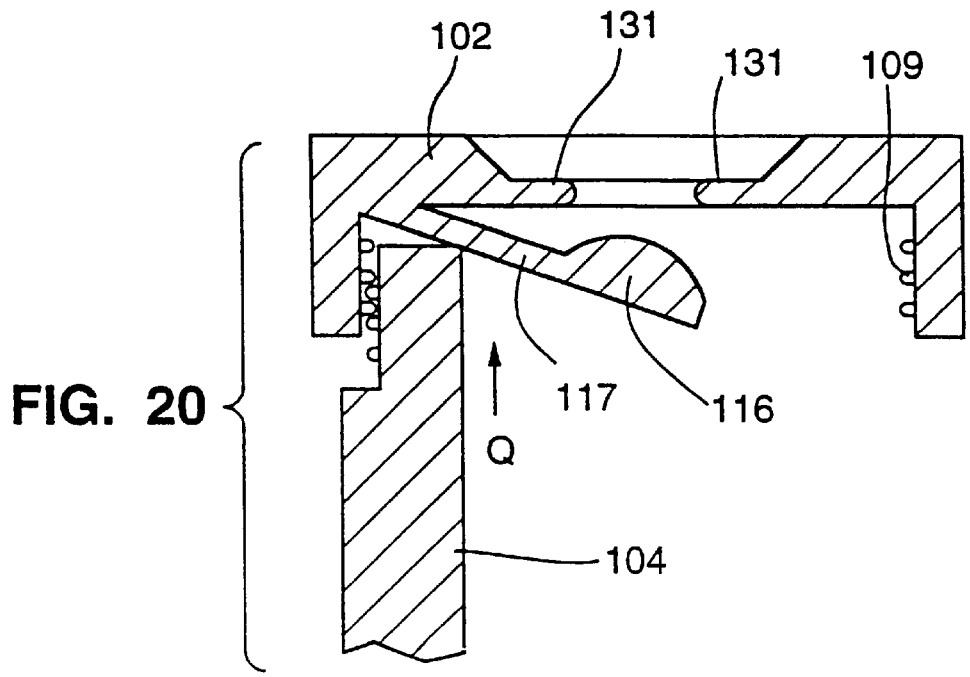
FIG. 20 is a side cross-sectional view of an alternative embodiment of the inventive disposable seal, which is molded as a single piece of elastomeric material (including a trap door portion).

Another class of embodiments of the inventive seal will be described with reference to FIG. 20. Disposable seal assembly 102 of FIG. 20 is a single molded piece of elastomeric material (including a trap door portion 116). Seal assembly 102 can be snapped over the proximal end of reusable cannula 104, with flange portion 109 of seal assembly 102 retaining assembly in the desired position over cannula 104's proximal end until a user removes seal assembly 102 from cannula 104. A flange portion 131 extends into the axial channel through seal assembly 102. Flange portion 131 (which is oriented in a plane perpendicular to the longitudinal axis of the axial channel) functions as an instrument seal (when an instrument is inserted through it) and also as a trap door seat (against which trap door portion 116 is biased to rest). Preferably, seal 102 is molded with trap door portion 116 (in the position shown in FIG. 20) at the end of extension portion 117. As shown in FIG. 20, portion 117 extends out from the rest of seal 102 at an angle relative to the plane of flange portion 131, so that trap door portion is not seated against flange 131.

FIG. 20 shows seal 102 while it is being snapped downward onto cannula 104, with seal 102 having freedom to be lowered further relative to cannula 104. As seal 102 is lowered relative to cannula 104 (beyond the position shown in FIG. 20), the upper end of cannula 104 will engage portion 117 and displace portion 117 upward until trap door portion 116 is seated in a closed position against flange 131. Once portion 116 reaches this closed position, the biasing force exerted by cannula 104 (through portion 117) on portion 116 will keep portion 116 in the closed position. In variations on the FIG. 20 embodiment, a trap door portion (corresponding to portion 116) is not integrally molded with the rest of the inventive seal assembly, but is attached to the inventive seal assembly (such as by an adhesive).

Another class of embodiments of the inventive instrument seal will be described with reference to FIGS. 10 and 11. Some such embodiments (e.g., the embodiment shown in FIG. 10) are designed with a circular flange around its outer periphery so that each can be removably snapped onto the end of a reusable cannula. Others of such embodiments are designed with a flange for removably snapping each of them onto an embodiment of the inventive seal assembly which includes a flapper valve (and such flapper valve assembly can be snapped onto the end of a reusable cannula). Others of such embodiments are integrally molded with an embodiment of the inventive seal assembly which includes a flapper valve (e.g., each such embodiment can replace the portion of the FIG. 2 assembly comprising flanges 31 and 32 and bumper 14b).

Figure 10:
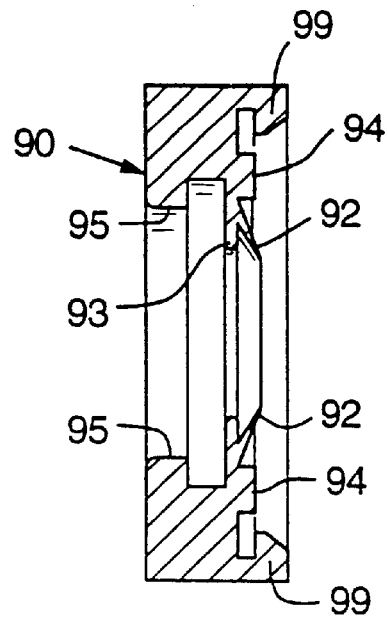
FIG. 10 is a side cross-sectional view of an instrument seal designed in accordance with an alternative embodiment of the invention.

Seal 90 of FIG. 10 includes a thick circular flange (bumper ring) 95, a thinner circular flange 93 (flange 93 is a sacrificial flange), and an even thinner circular flange 92 (flange 92 is thinner than both ring 95 and flange 93). Circular flange 99 around the outer periphery of seal 90 can be removably snapped onto the end of a cannula (e.g., into groove 12 of cannula 4, 6, 8, or 10 of FIG. 1). Alternatively, flange 99 can be removably snapped onto the end of an embodiment of the inventive seal assembly which includes a flapper valve. In the latter cases, seal 90 of FIG. 10 can function as an adaptor seal which provides a small-diameter instrument seal (implemented for example by flanges 92 and 93, if their diameters are sufficiently small) around a smaller diameter instrument than can be sealed by a larger-diameter instrument seal in the seal assembly to which seal 90 is snapped. In the following description of seal 90, we assume that in use, seal 90 is snapped onto the end of a cannula in a position relative to a cannula so that an instrument can be inserted into the cannula as follows: the instrument is translated from left to right in FIG. 10, so that the instrument first passes ring 95, then flange 93, then flange 92, and then enters the central channel within the cannula.

A central channel (oriented horizontally in FIG. 10) extends through seal 90, and seal 90 has rotational symmetry about this channel. Ring 95 does not extend as far radially into the central channel as does flange 93 or flange 92 (so that it does not interfere with the sealing function of flange 92). Instead, ring 95 functions to limit lateral movement of any instrument extending through the channel. Circular flange 93 functions as a sacrificial seal in the following sense. Flange 93 comes into contact with an instrument being inserted from left to right through the central channel through seal 90 before flange 92 does. If flange 93 is displaced (or even displaced and cut) by an instrument being so inserted (e.g., a sharp instrument), flange 92 will maintain a good fluid seal against the instrument (preventing fluid flow between flange 92 and the outer periphery of the instrument). Preferably, flange 92 extends farther into the channel than does flange 93 as shown and flange 92 is thinner than flange 93, so that if flange 93 is displaced (and possibly also cut) by the instrument being inserted, the displaced portion of flange 93 will fold toward flange 92, pushing flange 92 out of the path of the advancing instrument (so that flange 92 will avoid being cut by the instrument). Flange 92 is preferably oriented at an angle relative to flange 93 as shown (so that flange 92 extends toward the distal end of the cannula during use), to improve its ability to provide a good fluid seal with an instrument and to keep flanges 92 and 93 apart from each other (to prevent them from becoming overlapped in which case they might exert excessive drag force on the instrument). Alternatively, flanges 92 and 93 are parallel or substantially parallel to each other.

Seal 90 is preferably a single molded piece of elastic material, which has a thick ring portion 94 from which flanges 92 and 93 extend. The function of ring 94 will be described with reference to FIG. 11.

Figure 11:
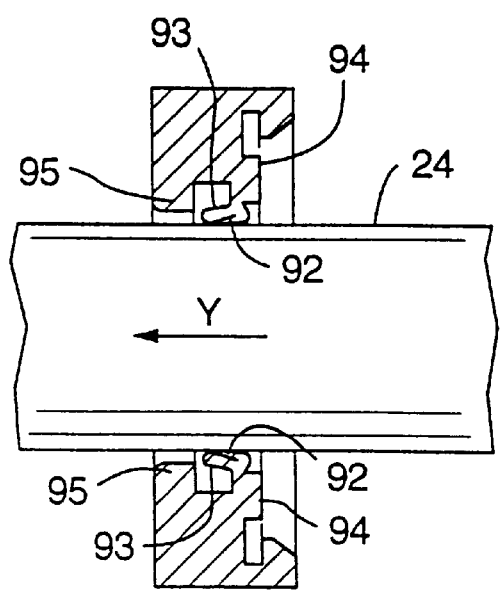
FIG. 11 is an enlarged view of a portion of the FIG. 10 apparatus, with medical instrument 24 being translated toward the left therethrough.

FIG. 11 shows instrument 24, which extends through the central channel through seal 90, in the process of being withdrawn from the seal (from right to left in FIG. 11). During this withdrawal process, it typically desired to maintain a good seal between flange 92 and the outer periphery of instrument 24. However, if the force exerted by instrument 24 on flange 92 bends and stretches flange 92 (and 93) too far toward ring 95 (in the direction of arrow Y shown in FIG. 11), flange 92 and sometimes also flange 93 can become trapped between instrument 24 and ring 95. This can substantially increase the drag exerted on the instrument, and/or it can break the seal between the instrument and flange 92, especially if flange 92 is torn as a result of the combined force of ring 95 and instrument 24 thereon. Ring 94 is provided to avoid such a break in the seal provided by flange 92. Specifically, ring 94 provides a stationary pivot point about which flanges 92 and 93 can pivot in response to instrument 24 as the instrument is withdrawn. Thus, ring 94 limits the range of motion of flange 92 enough to prevent flange 92 from reaching ring 95 (preventing flange 92 from becoming trapped between ring 95 and instrument 24).

As mentioned, seal 90 is designed to have its flange 99 removably snapped onto an appropriately shaped end portion of a rigid cannula. Preferably flange 99 is shaped so that ring 94 rests directly against the rigid cannula when seal 90 is mounted to the cannula. If so, the support provided by the cannula will prevent ring 94 from being displaced by insertion of an instrument into (or withdrawal of the instrument from) the channel through seal 90, and will thus ensure that ring 94 performs its intended function.

Figure 12:
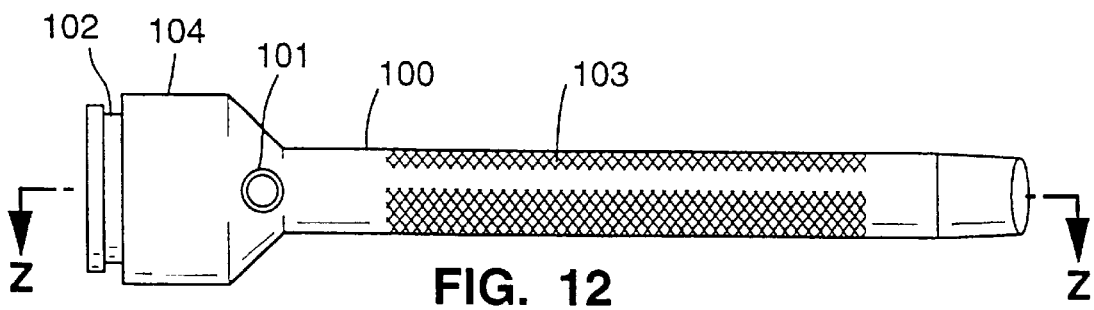
FIG. 12 is a side elevational view of a reusable cannula according to a preferred embodiment of the invention.
Figure 13:
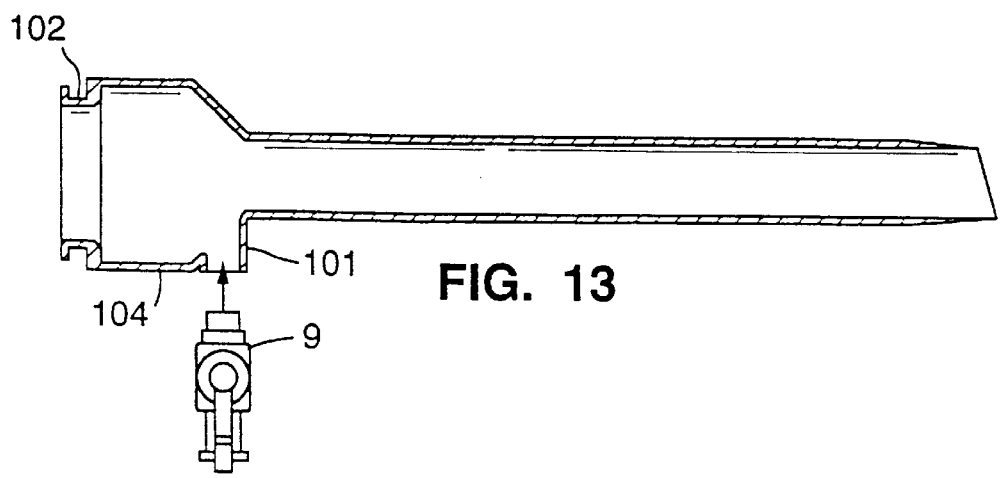
FIG. 13 is a cross-sectional view of cannula 100 of FIG. 12 (taken along line Z—Z of FIG. 12), with stopcock 9.

FIGS. 12 and 13 show a metal cannula 100, which is a preferred embodiment of the inventive reusable cannula. The proximal end of cannula 100 has an annular groove 102 for receiving a flange of one of the inventive disposable seal assemblies (so that the seal assembly can be removably snapped onto cannula 100). The distal portion of cannula 100 is a rigid, generally cylindrical tube whose bore has a circular cross-section. The bore of the tube defines a channel for accommodating an instrument such as an endoscope. In variations on this design, the bore of the cannula's distal portion can have any cross-sectional shape, but is sized and shaped to receive a medical instrument. The outer wall of cannula 100's distal portion has a grip portion 103. Preferably, grip portion 5 produced by scoring a cross-hatch pattern as shown in FIG. 12 (or a spiral pattern as shown in FIG. 1) into the outer metal surface of cannula 100.

An orifice 101 is machined (or otherwise manufactured) through large diameter portion 104 of cannula 100. A stopcock 9 can be inserted into orifice 101 as shown in FIG. 13. A source of insufflation gas can be connected to stopcock 9 at desired times during a medical procedure, and stopcock 9 can be opened (to allow gas to flow through orifice 101 into or out from cannula 100) or closed (to seal orifice 101).

Figure 23:
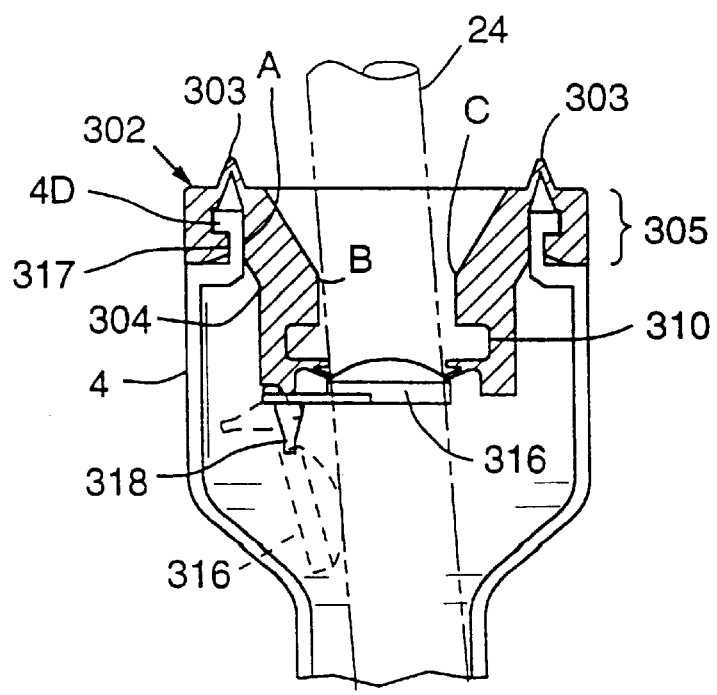
FIG. 23 is a side cross-sectional view of an alternative embodiment of the inventive seal, snapped onto the end of cannula 4 (of FIG. 1).

FIG. 23 is a side cross-sectional view of seal assembly 302 (an alternative embodiment of the inventive disposable seal assembly) snapped onto proximal end 4D of cannula 4 (of FIG. 1). Seal assembly 302 includes trap door 316, flexible barbed portions 318 on which door 316 is mounted, and flange 317 which is snapped into the cannula's annular groove (near proximal end 4D). Seal assembly 302 includes thin baffle membrane 303 (which is generally annular in shape), which separates bumper portion 304 of assembly 302 from outer rim portion 305 of assembly 302. Rim portion 305 is fixed relative to cannula 4 during use of the FIG. 23 apparatus. Membrane 303 is flexible, and thus allows bumper portion 304 to move (relative to fixed rim portion 305) in response to force exerted thereon by instrument 24.

During use of the FIG. 23 apparatus, instrument 24 is inserted through the central longitudinal channel through assembly 303 (which is oriented vertically in FIG. 23) so that the distal end of instrument 24 extends into the central channel through cannula 4, with at least a portion of the cylindrical surface of bumper portion 304 engaged with instrument 24 (as shown). Flange 310 is an instrument seal through which instrument 24 is inserted, and flange 310 prevents fluid flow through the channel around the outer periphery of instrument 24. When instrument 24 moves (e.g.

translates laterally toward the left side of FIG. 23) so that instrument 24 exerts a side loading force (toward the left in FIG. 23) on point B of the cylindrical surface of bumper portion 304, bumper portion 304 rotates about point A of bumper portion 304 (point A is the lowest point along the central longitudinal axis of seal assembly 302, in the plane of FIG. 23, of the surface of bumper portion 304 which engages cannula 4), thus pulling portion C of bumper portion 304 (on the opposite side of instrument 24 in the plane of FIG. 23) laterally toward point A (and slightly downward along the central longitudinal axis of seal assembly 302). This rotation of bumper portion 304 causes flange 303 to move in the direction of the lateral force exerted on point B (i.e., generally toward point A), thus enabling flange 303 to stay fully in contact with instrument 24, thus preserving a good fluid seal around the outer periphery of instrument 24 (despite the lateral motion of instrument 24). Seal assembly 302 should be designed so that point A is located above point B (along the central longitudinal axis of seal assembly 302), to enable bumper portion 304 to rotate in the described manner.

Also within the scope of the invention are methods for using any of the described embodiments of a cannula system including a reusable cannula and disposable seal (or seal assembly). One such method is a method for using a cannula system including a reusable cannula and a disposable seal assembly having a flange shaped for removable attachment to an end of the cannula, where the seal assembly includes a mounting portion made of elastomeric material and a trap door mounted to the mounting portion, the cannula has a first channel therethrough, and the seal assembly has a second channel therethrough, said method including the steps of:

(a) assembling the system by snapping the flange of the seal assembly into a groove of the cannula at said end of the cannula, so that the first channel is aligned with the second channel and the door is biased by the mounting portion into a closed position which seals the first channel;

(b) advancing an instrument in a first direction through the first channel, thereby displacing the door from the closed position to an open position and bending and stretching the mounting portion; and (c) withdrawing the instrument from the first channel in a second direction opposite the first direction, thus allowing the mounting portion to relax and thereby to return the door to the closed position.

Preferably, the mounting portion is an over-centered hinge for the door, in the sense that the door has a main portion for sealing the first channel (e.g., the hemispheric portion of door 16 of FIG. 4), an end portion about which the door pivots when displaced by the instrument (e.g., portion 16D of door 16 of FIG. 4), and an intermediate portion attached to a first portion of the mounting portion (the portion of door 16 which engages barbed portions 18 as shown in FIG. 2), wherein the end portion and the first portion are separated by a first distance (perpendicular to the central longitudinal axis Z of the channel) when the door is in the closed position (distance X in FIG. 2), and wherein the bending and stretching of the mounting portion during step (b) causes the end portion and the first portion to be separated by a second distance (perpendicular to the central longitudinal axis Z of the channel) when the door is in the open position, where the second distance is less than the first distance. The bending and stretching of the mounting portion during step (b) allows the end portion to move closer to the first portion, so that the end portion and the first portion are separated by the second distance when the door is in the open position.

Another example of a method for using a cannula system in accordance with the invention assumes that the system includes a cannula and a disposable seal assembly having a flange shaped for removable attachment to an end of the cannula, wherein the cannula has a first channel therethrough, the seal assembly has a second channel therethrough, and the seal assembly includes a sacrificial flange at a first location along the first channel and a sealing flange at a second location along the first channel. This method includes steps of:

(a) assembling the system by snapping the flange of the seal assembly into a groove of the cannula at said end of the cannula, so that the first channel is aligned with the second channel;

(b) advancing an instrument through the first channel until a tip of said instrument (which may be a sharp tip) engages and displaces (and possibly also cuts) a portion of the sacrificial flange, thereby causing the displaced portion of the sacrificial flange temporarily to displace a portion of the sealing flange away from the instrument; and (c) continuing to advance the instrument through the first channel until the tip passes the sacrificial seal and the sealing flange, while the sealing flange relaxes into engagement with an outer periphery of the instrument, thereby preventing fluid flow through the first channel around said outer periphery.

The foregoing is merely illustrative and explanatory of preferred embodiments of the inventive methods and apparatus. Various changes in the component sizes and shapes, and other details of the embodiments described herein may be within the scope of the appended claims.

What is claimed is:

1. A disposable seal assembly, including:

a body through which a channel extends to a distal end of the body;

a sacrificial flange having a first diameter and being positioned along the channel at a first location; and a sealing flange having a second diameter less than the first diameter and being positioned along the channel at a second location distal of the first location of the sacrificial flange, wherein at least one of the sacrificial flange and the sealing flange provides a seal around an instrument when the instrument is positioned in the channel;

the sacrificial flange being shaped so that in response to displacement of a portion of the sacrificial flange by the instrument while the instrument is inserted through the channel, the displaced portion of the sacrificial flange folds toward the sealing flange, thereby displacing a portion of the sealing flange to prevent the sealing flange from being cut by the instrument as the instrument continues translating through the channel the displaced portion of the sacrificial flange being thicker than the portion of the sealing flange;

the sealing flange protruding from the body at an angle relative to the sacrificial flange, so that the sealing flange extends in a direction away from the sacrificial flange; and the sacrificial flange being disposed generally in a plane extending radially of the channel.

2. The assembly of claim 1, also including:

a mounting flange protruding from the body, wherein the mounting flange is shaped for removably snapping the body onto a cannula.

3. A disposable seal assembly, including:

a body through which a channel extends to a distal end of the body;

a sacrificial flange having in a relaxed state an opening with a first diameter and being positioned along the channel at a first location;

a sealing flange having in a relaxed state a second diameter less than the first diameter of the sacrificial flange and being positioned along the channel at a second location distal of the first location, the sealing flange providing a seal around an instrument when the instrument is positioned in the channel; and the sacrificial flange being shaped so that in response to displacement of a portion of the sacrificial flange by the instrument as the instrument is inserted through the channel, the displaced portion of the sacrificial flange moves distally thereby displacing a portion of the sealing flange to prevent the sealing flange from being cut by the instrument as the instrument continues translating through the channel.

4. The disposable seal assembly recited in claim 3 wherein the sacrificial flange in its relaxed state is disposed generally in the plane extending transverse to the channel of the body.

5. The disposable seal assembly recited in claim 4 wherein the plane of the sacrificial flange extends generally radially of the channel of the body.

6. The disposable seal assembly recited in claim 5 further comprising:

a zero seal disposed distally of the sacrificial flange and the sealing flange and having properties for sealing the channel in the absence of an instrument positioned within the channel.

7. The disposable seal assembly recited in claim 6 wherein the zero seal includes a valve seat and a valve element forming a seal in the absence of an instrument in the channel;

a trap door providing the valve element and being pivotally mounted relative to the body to form a seal with a valve seat; and portions of the sealing flange providing the valve seat for the valve element.

8. A disposable seal assembly, including:

a body having a channel which extends between a proximal end and a distal end, the body including a flange for removably snapping the body onto a cannula;

a flexible extension protruding from the body;

a trap door having a generally rigid configuration and being mounted to the flexible extension, such that the flexible extension biases the rigid door into a closed position which seals the channel against a door seat and the flexible extension can move in response to displacement of the rigid door from the closed position by an instrument translating through the channel; and at least one instrument seal which provides the door seat for the trap door when the instrument is absent from the channel, and which seals the channel against the instrument when the instrument is positioned in the channel.

9. The assembly of claim 8, wherein the body, the flange, the flexible extension, and each said instrument seal are portions of a single piece of molded elastomeric material.

10. The assembly of claim 9, wherein the elastomeric material is a medical grade elastomer.

11. The assembly of claim 8, wherein the door is mounted to the flexible extension such that in response to displacement of the door into an improper position, the flexible extension exerts a restoring force on the door tending to reposition the door into said closed position.

12. The assembly of claim 11, wherein the body has an instrument seal portion against which the door rests when the door is in said closed position, and wherein the door is mounted to the flexible extension such that, in response to displacement of the door proximally through said instrument seal portion, the flexible extension does not tear, and direct manual force exerted by a user distally on the door, together with the restoring force exerted by the flexible extension on the door, is sufficient to reposition the door into said closed position.

13. The disposable seal assembly recited in claim 8, further comprising:

a sacrificial flange disposed proximally of the instrument seal for protecting the instrument seal.

14. The disposable seal assembly recited in claim 13 wherein the sacrificial flange is disposed generally in a plane transverse to the channel of the body.

15. The disposable seal assembly recited in claim 14 wherein the plane of the sacrificial flange extends radially of the channel of the body.

16. A disposable seal assembly, including:

a body through which a channel extends, wherein the body includes a flange shaped for removably snapping the body onto a cannula, and the body has a mounting portion, including;

a trap door mounted to the mounting portion of the body and movable between a first position wherein the door seals the channel against a door seat and a second position wherein the door opens the channel to facilitate instrument translation through the channel, the mounting portion having properties facilitating movement of the door over-center between the first position and the second position; and at least one instrument seal which provides the door seat for the trap door when the instrument is absent from the channel, and which seals the channel against the instrument when the instrument is positioned in the channel, wherein the body including the mounting portion, the flange, and each said instrument seal are portions of a single piece of molded elastomeric material.

17. The disposable seal assembly recited in claim 16, further comprising:

a sacrificial flange disposed proximally of the instrument seal to protect the instrument seal.

18. The disposable seal assembly recited in claim 17 wherein the sacrificial flange is disposed in a plane extending transverse to the channel of the body.

19. The disposable seal assembly recited in claim 18 wherein the plane of the sacrificial flange extends radially of the channel of the body.

20. A cannula system, comprising:

a reusable cannula having a first end; and a disposable seal assembly, comprising:

a body through which a channel extends, said body including a flange removably snapped onto the first end of the cannula;

a flexible extension which protrudes from the body;

a trap door having a rigid configuration and being mechanically joined to the flexible extension, so that the flexible extension biases the door against a door seat and into a closed position which seals the channel, and facilitates over-center displacement of the door from the closed position by an instrument translating through the channel; and at least one instrument seal which provides the door seat for the trap door when the instrument is absent from the channel, and forms the door seat for the trap door and seals the channel when the instrument is positioned in the channel.

21. The system of claim 20, wherein the body, the flange, the flexible extension, and each said instrument seal are portions of a single piece of molded elastomeric material.

22. The system of claim 21, wherein the cannula is made of metal.

23. A disposable seal assembly, including:

a body having a channel extending between a proximal end and a distal end, the body including a flange shaped for removably snapping the body onto a cannula;

at least one instrument seal disposed to seal the channel when an instrument is positioned within the channel;

a circumferential lip included in the instrument seal, the lip being radially expandable to accommodate instruments of different diameters;

a zero-closure valve disposed in the channel and having properties for blocking the channel when an instrument is not present within the channel, the zero-closure valve having a valve seat and a movable valve element;

a trap door comprising the movable valve element of the zero-closure valve, the trap door being movable between a first position wherein the trap door forms a seal with the valve seat to block the channel, and a second position wherein the trap door is spaced from the valve seat to permit translation of the instrument through the channel; and the lip of the instrument seal forming the valve seat of the zero-closure valve.

24. The seal assembly recited in claim 23, wherein the trap door moves over-center between the first position and the second position of the trap door.

25. The seal assembly recited in claim 23 wherein the trap door has a rigid configuration.

26. The seal assembly recited in claim 21 wherein the sacrificial flange extends generally radially of the channel and is thicker in configuration than the instrument seal.

27. The seal assembly recited in claim 23 further comprising:

a sacrificial flange disposed proximal of the at least one instrument seal and having properties for responding to a sharp tip of the instrument to temporarily move the at least one instrument seal from the path of the instrument in order to prevent damage to the instrument seal.

* * * * *